United States Patent [19]

Leinert et al.

[11] Patent Number: 4,927,834
[45] Date of Patent: May 22, 1990

[54] NEW 1,2-DIAMINO COMPOUNDS, PROCESSES FOR THEIR PREPARATION AND PHARMACEUTICAL COMPOSITIONS CONTAINING THEM

[75] Inventors: Herbert Leinert, Heppenheim; Christos Tsaklakidis, Weinheim; Gisbert Sponer, Laudenbach, all of Fed. Rep. of Germany

[73] Assignee: Boehringer Mannheim GmbH, Mannheim, Fed. Rep. of Germany

[21] Appl. No.: 230,946

[22] Filed: Aug. 11, 1988

[30] Foreign Application Priority Data

Aug. 11, 1987 [DE] Fed. Rep. of Germany ....... 3726633

[51] Int. Cl.$^5$ ..................... A61K 31/40; C07D 295/08
[52] U.S. Cl. ................................. 514/422; 514/428; 546/281; 546/334; 548/517; 548/525; 548/527; 548/526; 548/569; 549/495
[58] Field of Search ................ 548/569, 526; 514/428, 514/422

[56] References Cited

U.S. PATENT DOCUMENTS

| Re. 30,577 | 4/1981 | Busch et al. ........................ 548/569 |
| 3,962,238 | 6/1976 | Mauvernay et al. ............ 548/569 X |
| 4,620,015 | 10/1986 | Stiefel ................................. 548/547 |
| 4,645,778 | 2/1987 | Monteil et al. ................. 548/526 X |
| 4,727,072 | 2/1988 | Grous et al. ...................... 514/233.8 |
| 4,758,563 | 7/1988 | Grous et al. ...................... 544/148 X |

FOREIGN PATENT DOCUMENTS

| WO-A-8302274 | 7/1983 | European Pat. Off. |
| EP-A-0138684 | 4/1985 | European Pat. Off. |
| EP-A-0237191 | 9/1987 | European Pat. Off. |
| 2802864 | 7/1978 | Fed. Rep. of Germany |

*Primary Examiner*—Joseph Paul Brust
*Attorney, Agent, or Firm*—Armstrong, Nikaido, Marmelstein, Kubovcik & Murray

[57] ABSTRACT

The present invention provides compounds of the general formula:

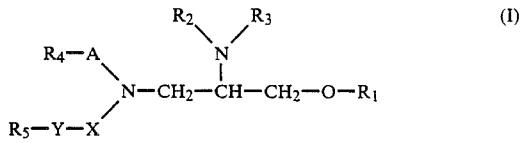

wherein $R_1$ is a straight-chained or branched $C_1$-$C_{12}$-alkyl radical which can be substituted by phenyl, naphthyl or a $C_3$-$C_7$-cycloalkyl radical; a straight-chained or branched $C_2$-$C_6$-alkenyl radical which can be substituted by a $C_3$-$C_7$-cycloalkyl radical or a phenyl or naphthyl radical; a $C_3$-$C_7$-cycloalkyl radical or a mono- or bicyclic aromatic radical which is unsubstituted or substituted one or more times, the substituents being $C_1$-$C_4$-alkyl, $C_1$-$C_4$-alkoxy, carboxyl or carbethoxy, $R_2$ and $R_3$, which can be the same or different, are straight-chained or branched, saturated or unsaturated $C_1$-$C_6$-alkyl radicals which are optionally substituted by hydroxyl, $C_1$-$C_3$-alkoxy or $C_1$-$C_3$-alkoxy-$C_1$-$C_3$-alkoxy or, together with the nitrogen atom to which they are attached, form a saturated or unsaturated ring which can contain further heteroatoms and is optionally substituted by a lower alkyl or lower alkoxy radical or by an oxygen atom, A is a valency bond or a straight-chained or branched alkylene radical containing up to 6 and preferably up to 3 carbon atoms, $R_4$ is a mono- or bicyclic aromatic or heteroaromatic radical which is unsubstituted or substituted one or more times, whereby the substituents are alkyl, $C_2$-$C_6$-alkenyl, alkoxy, $C_2$-$C_6$-alkenyloxy, hydroxyalkyl, $C_2$-$C_6$-alkylenedioxy, hydroxyalkoxy, alkoxyethoxy, alkylamino, dialkylamino, alkoxycarbonylethyloxy, alkylthio, alkylsulphinyl, alkylsulphonyl, alkylsulphonyloxy, carboxyl, alkoxycarbonyl, aminocarbonyl, mono- or dialkylaminocarbonyl, haloalkyl or cyano, as well as halogen atoms, such as chlorine, bromine or fluorine, X is a valency bond or a straight-chained or branched, saturated or unsaturated hydrocarbon radical containing up to 6 carbon atoms, Y is a valency bond or an oxygen atom and $R_5$ is a $C_3$-$C_7$-cycloalkyl radical or a mono- or bicyclic aromatic or heteroaromatic radical which is unsubstituted or substituted one or more times, the substituents being alkyl, alkoxy, $C_2$-$C_6$-alkenyloxy, aralkoxy, hydroxyl, hydroxyalkoxy, alkoxyalkoxy, alkoxycarbonylalkoxy, $C_1$-$C_2$-alkenylenedioxy, dialkylamino, alkylthio, alkylsulphinyl, alkyl-sulphonyl, alkylsulphonyloxy, hydroxyalkyl, carboxyl, alkoxycarbonyl, aminocarbonyl, mono- or dialkylaminocarbonyl or cyano, as well as halogen atoms, such as chlorine, bromine or fluorine, with the proviso that Y cannot be an oxygen atom when X is a valency bond and that when $R_1$ is a saturated hydrocarbon radical, X must be a radical with at least 2 carbon atoms; as well as the pharmacologically acceptable salts thereof and the optical isomers thereof.

The present invention also provides processes for the preparation of these 1,2-diamino compounds and pharmaceutical compositions containing them.

11 Claims, No Drawings

1,2-DIAMINO COMPOUNDS, PROCESSES FOR THEIR PREPARATION AND PHARMACEUTICAL COMPOSITIONS CONTAINING THEM

The present invention is concerned with new 1,2-diamino compounds, processes for the preparation thereof and pharmaceutical compositions containing them.

The new 1,2-diamino compounds according to the present invention are compounds of the general formula:

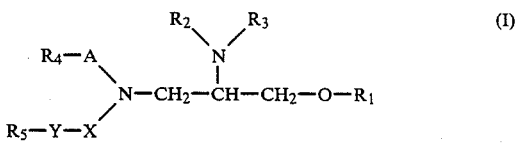

wherein $R_1$ is a straight-chained or branched $C_1$–$C_{12}$-alkyl radical which can be substituted by a phenyl, naphthyl or $C_3$–$C_7$-cycloalkyl radical, or is a straight-chained or branched $C_2$–$C_6$-alkenyl radical which can be substituted by a $C_3$–$C_7$-cycloalkyl radical or by a phenyl or naphthyl radical, or is a $C_3$–$C_7$-cycloalkyl radical or a mono- or bicyclic aromatic radical which is unsubtituted or substituted one or more times, in which the substituents can be $C_1$–$C_4$-alkyl, $C_1$–$C_4$-alkoxy, carboxyl or carbethoxy, $R_2$ and $R_3$, which can be the same or different, are straight-chained or branched, saturated or unsaturated $C_1$–$C_6$-alkyl radicals which can optionally be substituted by hydroxyl, $C_1$–$C_3$-alkoxy or $C_1$–$C_3$-alkoxy-$C_1$–$C_3$-alkoxy, or together with the nitrogen atom to which they are attached, form a saturated or unsaturated ring which can contain further heteroatoms and is optionally substituted by a lower alkyl radical, a lower alkoxy radical or an oxygen atom, A is a valency bond or a straight-chained or branched alkylene radical containing up to 6 and preferably up to 3 carbon atoms, $R_4$ is a mono- or bicyclic aromatic or heteroaromatic radical which is unsubstituted or substituted one or more times, in which the substituents are alkyl, $C_2$–$C_6$-alkenyl, alkoxy, $C_2$–$C_6$-alkenyloxy, hydroxyalkyl, $C_2$–$C_6$-alkylenedioxy, hydroxyalkoxy, alkoxyalkoxy, alkylamino, dialkylamino, alkoxycarbonylalkoxy, alkylthio, alkylsulphinyl, alkylsulphonyl, alkylsulphonyloxy, carboxyl, alkoxycarbonyl, aminocarbonyl, mono- or dialkylaminocarbonyl, haloalkyl or cyano groups, as well as halogen atoms, such as chlorine, bromine or fluorine, X is a valency bond or a straight-chained or branched, saturated or unsaturated hydrocarbon radical containing up to 6 carbon atoms, Y is a valency bond or an oxygen atom and $R_5$ is a $C_3$–$C_7$-cycloalkyl radical or a mono- or bicyclic aromatic or heteroaromatic radical which is unsubstituted or substituted one or more times, in which the substituents are alkyl, alkoxy, $C_2$–$C_6$-alkenyloxy, aralkoxy, hydroxyl, hydroxyalkoxy, alkoxyalkoxy, alkoxycarbonylalkoxy, $C_1$–$C_2$-alkylenedioxy, dialkylamino, alkylthio, alkylsulphinyl, alkylsulphonyl, alkylsulphonyloxy, hydroxyalkyl, carboxyl, alkoxycarbonyl, aminocarbonyl, mono- or dialkylaminocarbonyl or cyano, as well as halogen atoms, such as chlorine, bromine or fluorine, with the proviso that Y is not an oxygen atom when X is a valency bond and when $R_1$ is a saturated hydrocarbon X must be a radical containing at least 2 carbon atoms, and the pharmacologically acceptable salts thereof.

The $C_1$–$C_{12}$-alkyl radical $R_1$ is preferably methyl, ethyl, propyl, isopropyl, isobutyl, isoamyl, isohexyl, n̲-hexyl, n̲-octyl or n̲-dodecyl and especially isobutyl, isoamyl or isohexyl. As a rule, the $C_3$–$C_7$-cycloalkyl radical is cyclopentyl or cyclohexyl. When the alkyl radical is substituted, then the cycloalkylmethyl, benzyl and phenethyl radicals are preferred. Preferred $C_2$–$C_6$-alkenyl radicals are allyl, methallyl and isopentenyl. A substituted radical can be styryl or cinnamyl. Mono- and bicyclic aromatic radicals $R_1$, $R_4$ and $R_5$ are preferably phenyl, naphthyl, indanyl, indenyl and tetralinyl.

$R_2$ and $R_3$ preferably signify methyl, ethyl, propyl, allyl or methallyl. Rings which $R_2$ and $R_3$ can form together with the nitrogen atom to which they are attached are preferably pyrrolidine or piperidine rings and especially the pyrrolidine ring. The heteroatoms which the rings can contain are nitrogen, sulphur and oxygen. These include rings such as piperazine, morpholine and thiomorpholine. Substituents of the above-mentioned rings are especially $C_1$–$C_3$-alkyl and $C_1$–$C_3$-alkoxy radicals, for example methyl, ethyl, propyl, methoxy, ethoxy and propoxy. As a rule, the oxygen substituent, together with the carbon atom to which it is attached, represents a carbonyl group. Corresponding rings are, for example, the pyrrolidinone and piperidinone rings.

Heteroaromatic radicals $R_4$ and $R_5$ are preferably pyridyl, pyrimidinyl, pyrazinyl, thienyl, oxazolyl, pyrazolyl, imidazolyl, tetrazolyl, thiazolyl, iso-oxazolyl quinolyl, isoquinolyl, benzofuranyl, benzothienyl, benzothiazolyl, indolyl and furanyl and especially benzofuranyl, pyridyl, furanyl and thienyl.

The alkyl radicals, alone or in combination with other radicals of substituents $R_4$ and $R_5$ of the ring systems contain up to 6 and preferably up to 4 carbon atoms and are especially methyl radicals. The substitution can be single or multiple.

The compounds of general formula (I) according to the present invention can be prepared in known manner in that (a) a compound of the general formula:

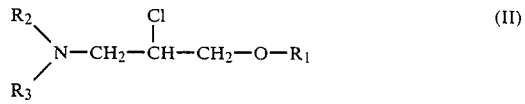

in which $R_1$, $R_2$ and $R_3$ have the above-given meanings, is reacted with a compound of the general formula:

in which A, X, Y, $R_4$ and $R_5$ have the above-given meanings; or (b) a compound of the general formula:

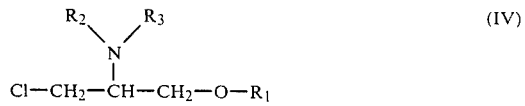

in which $R_1$, $R_2$ and $R_3$ have the above-given meanings, is reacted with a compound of general formula (III); or (c) a compound of the general formula:

$$B-CO-\underset{\underset{\displaystyle CH-CH_2-O-R_1}{|}}{\overset{\overset{\displaystyle R_2\diagdown \diagup R_3}{N}}{}} \quad (V)$$

in which $R_1$, $R_2$ and $R_3$ have the above-given meanings and B is a halogen atom or an alkoxy radical, is subjected to an amide formation reaction with a compound of general formula (III) and the compound obtained of general formula:

$$\underset{\underset{\displaystyle R_5-Y-X}{\diagup}}{\overset{\overset{\displaystyle R_4-A}{\diagdown}}{N}}-CO-\underset{\underset{\displaystyle CH-CH_2-O-R_1}{|}}{\overset{\overset{\displaystyle R_2\diagdown \diagup R_3}{N}}{}} \quad (VI)$$

in which $R_1$, $R_2$, $R_3$, $R_4$, $R_5$, A, X and Y have the above-given meanings, is reduced with a complex hydride or diborane.

The reaction of a compound of general formula (II) with a compound of general formula (III) to give a compound of general formula (I) according to the present invention takes place in known manner in an inert solvent, for example toluene, xylene or dimethylformamide, at a temperature of from 40° C. and the reflux temperature of the solvent in the presence of an alkaline condensation agent, for example sodium hydride or sodamide.

The compounds of general formula (II) can be prepared by reacting a compound of the general formula:

$$R_1OH \quad (VII)$$

in which $R_1$ has the above-given meaning, with epichlorohydrin in the presence of aqueous sodium hydroxide solution and of a phase transfer catalyst, for example tetrabutylammonium bromide, and the compound obtained of the general formula:

$$\underset{CH_2}{\overset{O}{\diagup \diagdown}}CH-CH_2-O-R_1 \quad (VIII)$$

in which $R_1$ has the above-given meaning, is reacted with an amine of the general formula:

$$R_2-NH-R_3 \quad (IX)$$

in which $R_2$ and $R_3$ have the above-given meanings and the compound obtained of the general formula:

$$\underset{\underset{\displaystyle R_3}{\diagup}}{\overset{\overset{\displaystyle R_2}{\diagdown}}{N}}-CH_2-\underset{\underset{\displaystyle}{|}}{\overset{\overset{\displaystyle OH}{|}}{CH}}-CH_2-O-R_1 \quad (X)$$

in which $R_1$, $R_2$ and $R_3$ have the above-given meanings, is reacted with thionyl chloride in an inert solvent to give a compound of general formula (II).

The reaction of a compound of general formula (IV) with a compound of general formula (III) to give a compound of general formula (I) according to the present invention takes place in an inert solvent, for example toluene or xylene, at a temperature of from 40° C. to the reflux temperature of the solvent in the presence of an alkaline condensation agent, for example sodium hydride or sodamide.

The compounds of general formula (IV) can be prepared by reducing a compound of the general formula:

$$RCO_2-\underset{\underset{\displaystyle CH-CH_2-O-R_1}{|}}{\overset{\overset{\displaystyle R_2\diagdown \diagup R_3}{N}}{}} \quad (XI)$$

in which $R_1$, $R_2$ and $R_3$ have the above-given meanings and R is an alkyl radical, with a complex hydride, for example lithium aluminum hydride, in an inert solvent in known manner to give a compound of the general formula:

$$HOH_2C-\underset{\underset{\displaystyle CH-CH_2-O-R_1}{|}}{\overset{\overset{\displaystyle R_2\diagdown \diagup R_3}{N}}{}} \quad (XII)$$

in which $R_1$, $R_2$ and $R_3$ have the above-given meanings and reacting this in an inert solvent with thionyl chloride to give a compound of general formula (IV).

The starting compounds of general formula (XI) can be prepared according to the process described in Federal Republic of Germany Patent Specification No. 28 02 864.

The reaction of a compound of general formula (V) with a compound of general formula (III) to give a compound of general formula (VI), as well as the reduction of this compound to a compound of general formula (I) according to the present invention, takes place according to processes known from the literature.

The compounds of general formula (V), in which B is a halogen atom, can be prepared by hydrolysing a compound of general formula (XI) and reacting the compound obtained of the general formula:

$$HOOC-\underset{\underset{\displaystyle CH-CH_2-O-R_1}{|}}{\overset{\overset{\displaystyle R_2\diagdown \diagup R_3}{N}}{}} \quad (XIII)$$

in which $R_1$, $R_2$ and $R_3$ have the above-given meanings, with a halogenation agent, for example thionyl chloride, in an inert solvent.

The compounds of general formula (III) can be prepared in that, with maintenance of the above-given definitions for A, X, Y, $R_4$ and $R_5$ (a) a compound of the general formula:

$$R_4A-NH_2$$

is reacted with a compound of the general formula:

$$R_5-Y-COCl$$

and the amide obtained of the general formula:

$$R_4-A-NH-CO-Y-R_5$$

is reduced with a complex hydride or diborane; or (β) a compound of the general formula:

$$R_4-A'-CO-Cl$$

in which A' is an alkyl radical with up to 5 and preferably 1 or 2 carbon atoms, is reacted with a compound of the general formula:

$$R_5-Y-X-NH_2$$

and the amide obtained of the general formula:

$$R_4-A'-CO-NH-X-Y-R_5$$

is reduced with a complex hydride or diborane; or (γ) by reductive amination of a carbonyl compound of the general formula:

$$R_5-Y-X'-CO-Z$$

in which Z is a hydrogen atom or an alkyl radical and X' is a saturated or unsaturated, straight-chained or branched alkyl radical, X' always having one carbon atom less than X, with an amine of the general formula:

$$R_4ANH_2$$

or (δ) by reductive amination of a compound of the general formula:

$$R_4A'-CO-V$$

in which V is a hydrogen atom or an alkyl radical and A' is a saturated or unsaturated, straight-chained or branched alkyl radical, A' always having one carbon atom less than A, with a compound of the general formula:

$$R_5YX-NH_2$$

The compounds of general formula (I) according to the present invention possess an asymmetric carbon atom. Therefore, the present invention also includes racemates and the optically-active forms of the compounds of general formula (I) according to the present invention, as well as processes for the preparation thereof.

The optically-active compounds can be prepared from their racemic mixtures by known methods via diastereomeric salts. For the racemate resolution there can be used, for example, tartaric acid, malic acid, camphoric acid, camphorsulphonic acid or dibenzoyltartaric acid.

For the conversion of the compounds of general formula (I) into their pharmacologically acceptable salts, these are reacted, preferably in an organic solvent, with the equivalent amount of an inorganic or organic acid, for example hydrochloric acid, hydrobromic acid, phosphoric acid, sulphuric acid, acetic acid, salicylic acid, citric acid, benzoic acid, naphthoic acid, o-acetoxybenzoic acid, adipic acid, maleic acid, oxalic acid, fumaric acid or cyclamic acid.

The compounds of general formula (I) according to the present invention possess valuable pharmacological properties. They are characterised especially by a blood vessel-relaxing action and can, therefore, be used for the therapy of heart-circulatory diseases.

The new compounds of general formula (I) according to the present invention and the salts thereof can be administered enterally or parenterally in liquid or solid form. As injection medium it is preferred to use water which contains the additives usual in the case of injection solutions, such as stabilising agents, solubilising agents or buffers. Such additives include, for example, tartrate and citrate buffers, ethanol, complex formers (such as ethylenediamine-tetraacetic acid and its non-toxic salts) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

Besides the compounds described in the following Examples, the following compounds are also especially preferred.

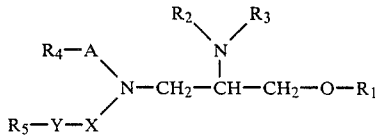

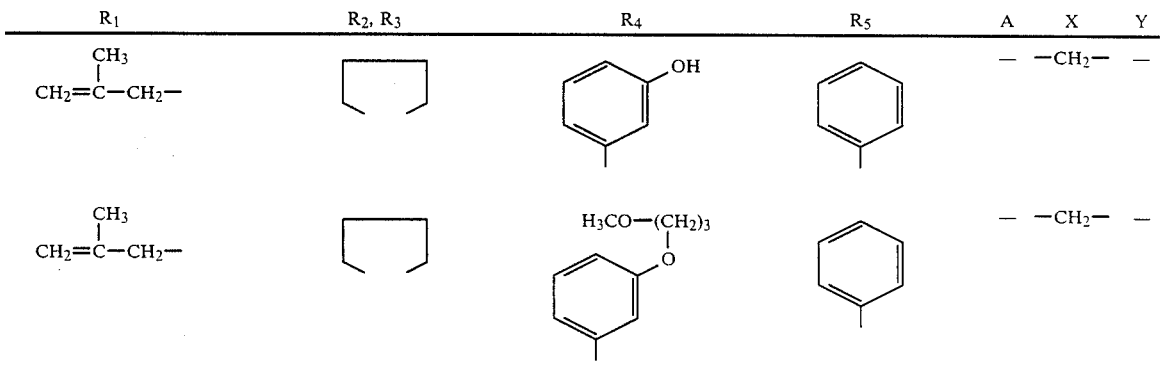

-continued $$R_4-A-N(R_5-Y-X)-CH_2-CH(N(R_2)(R_3))-CH_2-O-R_1$$

| $R_1$ | $R_2, R_3$ | $R_4$ | $R_5$ | A | X | Y |
|---|---|---|---|---|---|---|
| $CH_2=C(CH_3)-CH_2-$ | (pyrrolidine) | 3-$CF_3$-phenyl | phenyl | — | $-CH_2-$ | — |
| $CH_2=C(CH_3)-CH_2-$ | (pyrrolidine) | 4-($OCH_2-CO_2Et$)-phenyl | phenyl | — | $-CH_2-$ | — |
| $CH_2=C(CH_3)-CH_2-$ | (pyrrolidine) | 2-CN-phenyl | phenyl | — | $-CH_2-$ | — |
| $CH_2=C(CH_3)-CH_2-$ | (pyrrolidine) | phenyl | 4-($OCH_2CH=CH_2$)-phenyl | — | $-CH_2-$ | — |
| $CH_2=C(CH_3)-CH_2-$ | (pyrrolidine) | phenyl | 4-($OCH_2C_6H_5$)-phenyl | — | $-CH_2-$ | — |
| $CH_2=C(CH_3)-CH_2-$ | (pyrrolidine) | phenyl | 4-OH-phenyl | — | $-CH_2-$ | — |
| $CH_2=C(CH_3)-CH_2-$ | (pyrrolidine) | phenyl | 4-$SO_2CH_3$-phenyl | — | $-CH_2-$ | — |
| $CH_2=C(CH_3)-CH_2-$ | (pyrrolidine) | phenyl | 4-C(O)$NH_2$-phenyl | — | $-CH_2-$ | — |
| $CH_2=C(CH_3)-CH_2-$ | (pyrrolidine) | phenyl | 3-($(CH_2)_2OCH_3$)-phenyl | — | $-CH_2-$ | — |

-continued

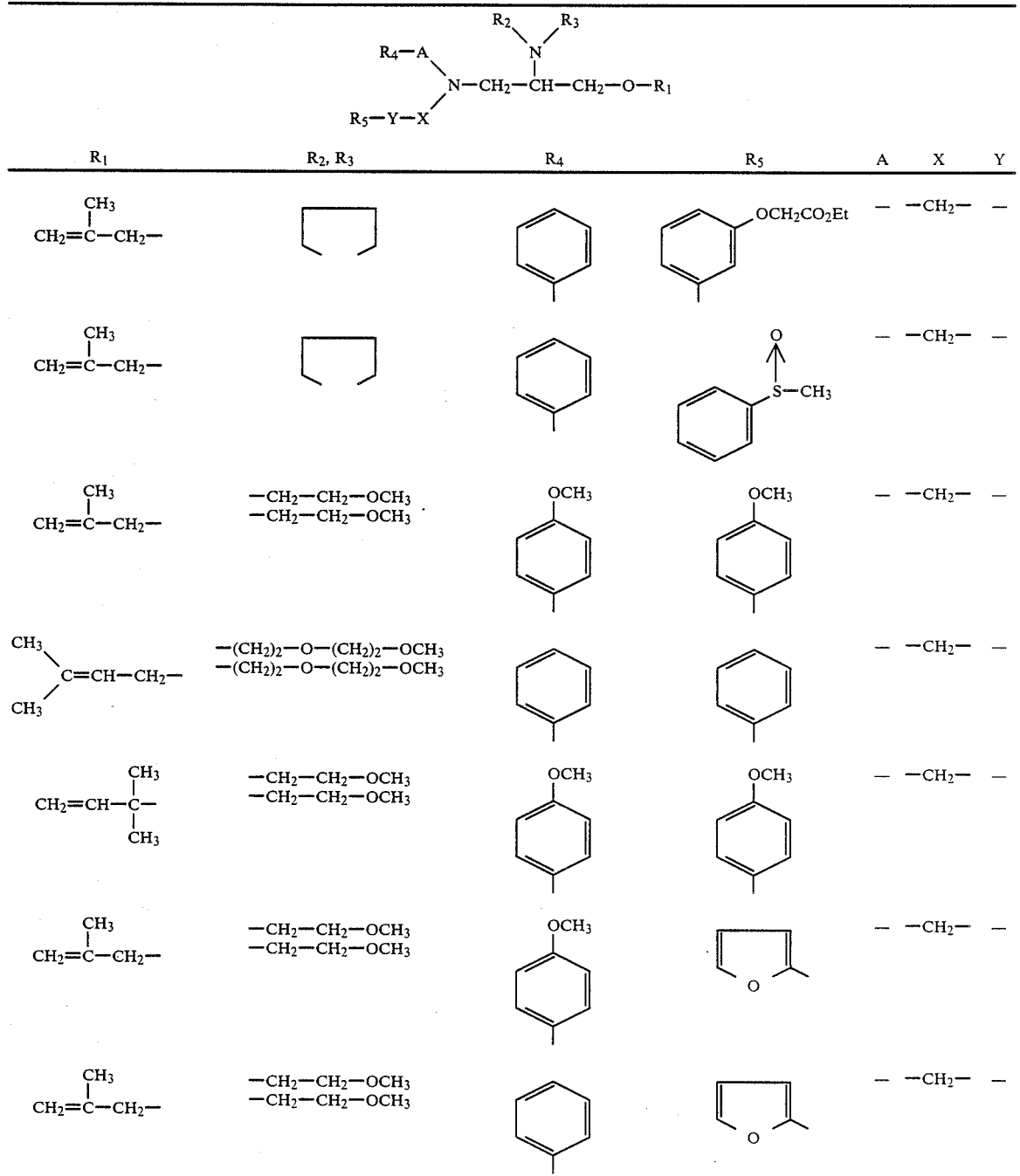

The following Examples are given for the purpose of illustrating the present invention:

Example 1.
2-(N-Pyrrolidino)-3-isobutoxy-N-phenyl-N-(2-phenyl-ethyl-propylamine oxalate.

6.3 g. N-phenyl-N-(2-phenylethyl)-amine, together with 7.7 g. 2-chloro-1-isobutoxy-3-(N-pyrrolidino)-propane are dissolved in 50 ml. anhydrous toluene. 5.8 g. Sodium hydride (50% oily suspension) are added thereto and the mixture is heated under reflux for 2 hours. It is then cooled, the mixture is poured on to water and the organic phase is separated off. The aqueous phase is extracted again with toluene. The combined organic phases are washed with water, dried over anhydrous sodium sulphate and evaporated. The residue is purified by chromatography on a silica gel column (elution agent methylene chloride/2% methanol).

The appropriate column fractions are evaporated. The residue is dissolved in ethyl acetate and the solution mixed with a solution of oxalic acid in ethyl acetate. The precipitate is filtered off and again recrystallised from ethyl acetate. There are obtained 2.1 g. 2-(N-pyrrolidino)-3-isobutoxy-N-phenyl-N-(2-phenylethyl)-propylamine oxalate; m.p. 95°–96° C.

The halo compounds of general formula (II) required as starting materials are prepared analogously to 2-chloro-1-allyloxy-3-N-pyrrolidinopropane, the preparation of which is described in the following by way of example:

A mixture of 50 g. allyl alcohol, 160 ml. concentrated aqueous sodium hydroxide solution, 230 g. epichlorohydrin and 2 g. tetrabutylammonium bromide is stirred for 3 hours at 45° C. The mixture is then diluted with water and extracted with ethyl acetate. The organic phase is washed with water, dried over anhydrous sodium sulphate and evaporated. The residue is distilled in a vacuum to give 67 g. 3-allyloxy-1,2-epoxypropane; b.p. 78° C./56 mm.Hg. This is dissolved in 80 ml. ethanol and mixed dropwise, while stirring, with a solution of 86 ml. pyrrolidine in 80 ml. ethanol. After completion of the addition, stirring is continued for 1 hour at 70° C., the mixture is evaporated and the residue is distilled in a vacuum to give 70 g. 2-hydroxy-1-allyloxy-3-N-pyrrolidinopropane; b.p. 75° C./$10^{-2}$ mm Hg.

60 g. 2-Hydroxy-1-allyloxy-3-N-pyrrolidinopropane are dissolved in 120 ml. dichloroethane and the solution mixed dropwise, while stirring, with 26 ml. thionyl chloride. After completion of the addition, stirring is continued for 2 hours at 70° C., the mixture is cooled, mixed with water, the pH value is adjusted with aqueous sodium hydroxide solution to 10 and the organic phase is separated off. This is dried over anhydrous sodium sulphate and evaporated. The residue is purified by column chromatography to give 44 g. 2-chloro-1-allyloxy-3-N-pyrrolidinopropane as an oily product.

The following compounds are prepared in an analogous way:

| No. | R₁ | R₂, R₃ | R₄ | R₅ | A | X | Y | |
|---|---|---|---|---|---|---|---|---|
| 2 | $(CH_3)_2-CH-CH_2-$ |  |  |  (phenyl) | — | $-(CH_2)_2-$ | — | Oxalate 95–96° C. ethyl acetate |
| 3 | $(CH_3)_2-CH-CH_2-$ |  |  |  (4-OCH₃ phenyl) | — | $-(CH_2)_2-$ | — | Fumarate 103–104° C. ethyl acetate |
| 4 | $(CH_3)_2-CH-CH_2-$ |  |  |  (3,4-diOCH₃ phenyl) | — | $-(CH_2)_2-$ | — | Oxalate 147–148° C. ethyl acetate |
| 5 | $(CH_3)_2-CH-CH_2-$ |  |  |  (4-Cl phenyl) | — | $-(CH_2)_2-$ | — | Oxalate 134° C. ethyl acetate |
| 6 | $(CH_3)_2-CH-CH_2-$ |  |  | phenyl | — | $-(CH_2)_2-$ | O | Fumarate 94–96° C. ethyl acetate |

-continued $$R_5-Y-X \diagdown N-CH_2-CH-CH_2-O-R_1 \diagup R_4-A \diagup \diagdown N \diagup R_2 R_3$$

| No. | R₁ | R₂, R₃ | R₄ | R₅ | A | X | Y | |
|---|---|---|---|---|---|---|---|---|
| 7 | (CH₃)₂—CH—CH₂— | pyrrolidine | phenyl | 4-OCH₃-phenyl | — | —(CH₂)₂— | O | Fumarate 134° C. ethyl acetate |
| 8 | (CH₃)₂—CH—CH₂— | pyrrolidine | phenyl | phenyl | — | —(CH₂)₃— | — | Oxalate 96-97° C. ethyl acetate |
| 9 | (CH₃)₂—CH—CH₂— | pyrrolidine | phenyl | 4-OCH₃-phenyl | — | —(CH₂)₃— | — | Oxalate 112-113° C. ethyl acetate |
| 10 | (CH₃)₂—CH—CH₂— | pyrrolidine | phenyl | 2-thienyl | — | —(CH₂)₂— | — | Oxalate 95-96° C. ethyl acetate |
| 11 | (CH₃)₂—CH—CH₂— | pyrrolidine | phenyl | 2-pyridyl | — | —(CH₂)₂— | — | oil m/e 380 |
| 12 | (CH₃)₂—CH—CH₂— | pyrrolidine | phenyl | phenyl | CH₂— | —(CH₂)₂— | — | oil m/e 394 |

-continued $$R_4-A \diagdown N-CH_2-CH-CH_2-O-R_1$$
$$R_5-Y-X \diagup \qquad N \diagdown R_3$$
$$\qquad \qquad \qquad R_2$$

| No. | R₁ | R₂, R₃ | R₄ | R₅ | A | X | Y | |
|---|---|---|---|---|---|---|---|---|
| 13 | (CH₃)₂—CH—CH₂— | (pyrrolidine) | 3-methylpyridinyl | 4-OCH₃-phenyl | — | —(CH₂)₂— | — | oil m/e 425 |
| 14 | CH₂=CH—CH₂— | (pyrrolidine) | phenyl | phenyl | — | —CH₂— | — | Oxalate 152–153° C. ethyl acetate |
| 15 | CH₂=C(CH₃)—CH₂— | (pyrrolidine) | phenyl | phenyl | — | —CH₂— | — | Oxalate 159–161° C. Isopropanol |
| 16 | CH₂=C(CH₃)—CH₂— | (pyrrolidine) | 4-OCH₃-phenyl | phenyl | — | —CH₂— | — | Oxalate 128–130° C. ethyl acetate |
| 17 | CH₂=C(CH₃)—CH₂— | (pyrrolidine) | 4-CH₃-phenyl | phenyl | — | —CH₂— | — | Oxalate 152° C. ethyl acetate |

-continued $$R_4-A-N-CH_2-CH-CH_2-O-R_1$$
$$\phantom{R_4-A-}|\phantom{N-CH_2-CH}|$$
$$\phantom{R_4-A-N-CH_2-C}N_{R_2}^{R_3}$$
$$R_5-Y-X$$

| No. | R₁ | R₂, R₃ | R₄ | R₅ | A | X | Y | |
|---|---|---|---|---|---|---|---|---|
| 18 | CH₂=C(CH₃)—CH₂— | ⟨ | 4-(N(CH₃)₂)—C₆H₄— | C₆H₅— | — | —CH₂— | — | oil m/e 407 |
| 19 | CH₂=C(CH₃)—CH₂— | ⟨ | 4-(OCH₂—CH=CH₂)—C₆H₄— | C₆H₅— | — | —CH₂— | — | oil m/e 420 |
| 20 | CH₂=C(CH₃)—CH₂— | ⟨ | 4-(CO₂Et)—C₆H₄— | C₆H₅— | — | —CH₂— | — | oil m/e 436 |
| 21 | CH₂=C(CH₃)—CH₂— | ⟨ | 4-(CO₂H)—C₆H₄— | C₆H₅— | — | —CH₂— | — | 159° C. ethyl acetate |
| 22 | CH₂=C(CH₃)—CH₂— | ⟨ | 4-(CH₂OH)—C₆H₄— | C₆H₅— | — | —CH₂— | — | oil m/e 394 |

-continued $$R_4-A \underset{R_5-Y-X}{\overset{R_2\diagdown N \diagup R_3}{N-CH_2-CH-CH_2-O-R_1}}$$

| No. | $R_1$ | $R_2, R_3$ | $R_4$ | $R_5$ | A | X | Y | |
|---|---|---|---|---|---|---|---|---|
| 23 | CH$_2$=C(CH$_3$)—CH$_2$— |  | 4-CONH$_2$—C$_6$H$_4$— 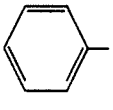 | C$_6$H$_5$— 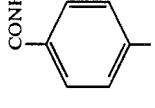 | — | —CH$_2$— | — | oil m/e 407 |
| 24 | CH$_2$=C(CH$_3$)—CH$_2$— |  | 3,4-methylenedioxyphenyl  | C$_6$H$_5$— 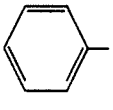 | — | —CH$_2$— | — | Oxalate 125–126° C. ethyl acetate |
| 25 | CH$_2$=C(CH$_3$)—CH$_2$— | 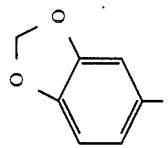 | 3-SCH$_3$—C$_6$H$_4$—  | C$_6$H$_5$—  | — | —CH$_2$— | — | Oxalate 114–115° C. ethyl acetate |
| 26 | CH$_2$=C(CH$_3$)—CH$_2$— | 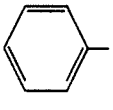 | C$_6$H$_5$—SO$_2$— 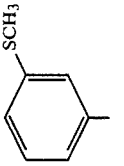 | C$_6$H$_5$—  | — | —CH$_2$— | — | oil m/e 442 |
| 27 | CH$_2$=C(CH$_3$)—CH$_2$— |  | 2-F—C$_6$H$_4$— 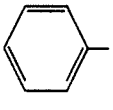 | C$_6$H$_5$— 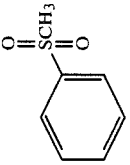 | — | —CH$_2$— | — | Oxalate 173–174° C. ethyl acetate |

-continued $$R_4-A \diagdown N-CH_2-CH-CH_2-O-R_1 \diagup R_5-Y-X \quad \diagup N \diagdown R_2 R_3$$

| No. | R₁ | R₂, R₃ | R₄ | R₅ | A | X | Y | |
|---|---|---|---|---|---|---|---|---|
| 28 | CH₂=C(CH₃)—CH₂— | (pyrrolidine) | 3,4-dichlorophenyl | phenyl | — | —CH₂— | — | Oxalate 192–193° C. ethyl acetate |
| 29 | CH₂=C(CH₃)—CH₂— | (pyrrolidine) | 3,4-dimethoxyphenyl | phenyl | — | —CH₂— | — | oil m/e 424 |
| 30 | CH₂=C(CH₃)—CH₂— | (pyrrolidine) | 3-methoxy-4-methylphenyl | phenyl | — | —CH₂— | — | oil m/e 408 |
| 31 | CH₂=C(CH₃)—CH₂— | (pyrrolidine) | benzofuran-5-yl | phenyl | — | —CH₂— | — | Oxalate 135–136° C. Isopropanol |
| 32 | CH₂=C(CH₃)—CH₂— | (pyrrolidine) | 3-(methylsulfinyl)phenyl | phenyl | — | —CH₂— | — | oil m/e 426 |

-continued $$\begin{array}{c} R_2 \diagdown \phantom{N} \diagup R_3 \\ \phantom{xxx} N \\ R_4-A \diagup \phantom{N} \diagdown N-CH_2-CH-CH_2-O-R_1 \\ \phantom{xxxxxxxxxxxxxx} | \\ \phantom{xxxxxxxxxxx} R_5-Y-X \end{array}$$

| No. | $R_1$ | $R_2, R_3$ | $R_4$ | $R_5$ | A | X | Y | |
|-----|-------|------------|-------|-------|---|---|---|---|
| 33 | $CH_2=\overset{CH_3}{\underset{\|}{C}}-CH_2-$ |  |  |  | — | $-CH_2-$ | — | oil m/e 411 |
| 34 | $CH_2=\overset{CH_3}{\underset{\|}{C}}-CH_2-$ |  |  |  | — | $-CH_2-$ | — | Oxalate 128–130° C. ethyl acetate |
| 35 | $CH_2=\overset{CH_3}{\underset{\|}{C}}-CH_2-$ |  |  |  | — | $-CH_2-$ | — | oil m/e 382 |
| 36 | $CH_2=\overset{CH_3}{\underset{\|}{C}}-CH_2-$ | | | | — | $-CH_2-$ | — | oil m/e 398 |
| 37 | $CH_2=\overset{CH_3}{\underset{\|}{C}}-CH_2-$ | | |   | — | $-CH_2-$ | — | oil m/e 408 |

-continued $$\begin{array}{c} R_2 \diagdown \phantom{xxx} R_3 \\ N \\ R_4-A\diagup \phantom{xxxxx} \diagdown N-CH_2-CH-CH_2-O-R_1 \\ R_5-Y-X\diagup \end{array}$$

| No. | R₁ | R₂, R₃ | R₄ | R₅ | A | X | Y | |
|---|---|---|---|---|---|---|---|---|
| 38 | CH₂=C(CH₃)—CH₂— | ⌐⌐ | —C₆H₅ | 4-CH₃—C₆H₄— | — | —CH₂— | — | oil m/e 378 |
| 39 | CH₂=C(CH₃)—CH₂— | ⌐⌐ | —C₆H₅ | 4-SCH₃—C₆H₄— | — | —CH₂— | — | oil m/e 410 |
| 40 | CH₂=C(CH₃)—CH₂— | ⌐⌐ | —C₆H₅ | 4-CO₂Et—C₆H₄— | — | —CH₂— | — | oil m/e 436 |
| 41 | CH₂=C(CH₃)—CH₂— | ⌐⌐ | —C₆H₅ | 4-CO₂H—C₆H₄— | — | —CH₂— | — | oil m/e 408 |
| 42 | CH₂=C(CH₃)—CH₂— | ⌐⌐ | —C₆H₅ | 4-CH₂OH—C₆H₄— | — | —CH₂— | — | oil m/e 394 |

-continued

| No. | R₁ | R₂, R₃ | R₄ | R₅ | A | X | Y | |
|---|---|---|---|---|---|---|---|---|
| 43 | CH₂=C(CH₃)−CH₂− | (pyrrolidine) | phenyl | indanyl | — | — | — | oil m/e 390 |
| 44 | CH₂=C(CH₃)−CH₂− | (pyrrolidine) | phenyl | tetrahydronaphthyl | — | — | — | oil m/e 402 |
| 45 | CH₂=C(CH₃)−CH₂− | (pyrrolidine) | phenyl | 2-furyl | — | −CH₂− | — | Oxalate 130–131° C. ethyl acetate |
| 46 | CH₂=C(CH₃)−CH₂− | (pyrrolidine) | phenyl | 2-thienyl | — | −CH₂− | — | Oxalate 135–136° C. ethyl acetate |
| 47 | CH₂=C(CH₃)−CH₂− | (pyrrolidine) | phenyl | phenyl | — | −(CH₂)₂− | — | Oxalate 79° C. ethyl acetate |
| 48 | CH₂=C(CH₃)−CH₂− | (pyrrolidine) | phenyl | 4-methoxyphenyl | — | −(CH₂)₂− | — | Oxalate 125–126° C. ethyl acetate |

-continued $$R_4-A \underset{R_5-Y-X}{\overset{R_2\ R_3}{\underset{|}{N}-CH_2-CH-CH_2-O-R_1}}$$

| No. | R₁ | R₂, R₃ | R₄ | R₅ | A | X | Y | |
|---|---|---|---|---|---|---|---|---|
| 49 | CH₂=C(CH₃)—CH₂— | ⌐⌐ | phenyl | 4-OCH₃-phenyl | — | —(CH₂)₃— | — | Fumarate 127° C. ethyl acetate |
| 50 | CH₂=C(CH₃)—CH₂— | ⌐⌐ | phenyl | 2-OCH₃-phenyl | — | —(CH₂)₂— | O | Oxalate 118–119° C. ethyl acetate |
| 51 | CH₂=C(CH₃)—CH₂— | ⌐⌐ | phenyl | phenyl | — | —(CH₂)₃— | — | Oxalate 130–131° C. ethyl acetate |
| 52 | CH₂=C(CH₃)—CH₂— | ⌐⌐ | phenyl | 2-methyl-pyridyl | — | —CH₂— | — | oil m/e 365 |
| 53 | CH₂=C(CH₃)—CH₂— | ⌐⌐ | phenyl | 2,5-dimethyl-furyl | — | —CH₂— | — | oil m/e 368 |
| 54 | CH₂=C(CH₃)—CH₂— | ⌐⌐ | 3-OCH₃-phenyl | 4-OCH₃-phenyl | — | —CH₂— | — | oil m/e 424 |

-continued $$R_4-A\underset{\underset{R_5-Y-X}{|}}{N}-CH_2-CH-CH_2-O-R_1$$
$$\phantom{xxxxxxxxx}|$$
$$\phantom{xxxxxxxxxx}N{\overset{R_3}{\underset{R_2}{\diagup}}}$$

| No. | R$_1$ | R$_2$, R$_3$ | R$_4$ | R$_5$ | A | X | Y | |
|---|---|---|---|---|---|---|---|---|
| 55 | CH$_2$=C(CH$_3$)−CH$_2$− | ⌐⌙ | C$_6$H$_5$ | C$_6$H$_5$ | — | −(CH$_2$)$_2$− | O | Oxalate 118–120° C. |
| 56 | CH$_2$=C(CH$_3$)−CH$_2$− | ⌐⌙ | 4-OCH$_3$-C$_6$H$_4$ | 4-OCH$_3$-C$_6$H$_4$ | — | −CH$_2$− | — | oil m/e 424 |
| 57 | CH$_2$=C(CH$_3$)−CH$_2$− | ⌐⌙ | 4-OCH$_3$-C$_6$H$_4$ | 4-OCH$_3$-C$_6$H$_4$ | — | −(CH$_2$)$_2$− | — | Oxalate 97–98° C. ethyl acetate |
| 58 | CH$_2$=C(CH$_3$)−CH$_2$− | ⌐⌙ | 4-OCH$_3$-C$_6$H$_4$ | 4-OCH$_3$-C$_6$H$_4$ | — | −(CH$_2$)$_2$− | O | Oxalate 93–95° C. ethyl acetate |
| 59 | CH$_2$=C(CH$_3$)−CH$_2$− | ⌐⌙ | 4-OCH$_3$-C$_6$H$_4$ | 4-OCH$_3$-C$_6$H$_4$ | — | −(CH$_2$)$_3$− | — | oil m/e 452 |

-continued $$R_4-A \diagdown \diagup R_2 \atop R_5-Y-X \diagup N-CH_2-CH(NR_2R_3)-CH_2-O-R_1$$

| No. | R1 | R2, R3 | R4 | R5 | A | X | Y | |
|---|---|---|---|---|---|---|---|---|
| 60 | CH$_2$=C(CH$_3$)—CH$_2$— | pyrrolidine | Ph | Ph | — | —(CH$_2$)$_4$— | — | Oxalate 92–95° C. |
| 61 | CH$_2$=C(CH$_3$)—CH$_2$— | pyrrolidine | Ph | 4-OCH$_3$-C$_6$H$_4$— | —CH$_2$— | —CH$_2$— | — | oil m/e 408 |
| 62 | CH$_2$=C(CH$_3$)—CH$_2$— | pyrrolidine | Ph | 4-Cl-C$_6$H$_4$— | —CH$_2$— | —CH$_2$— | — | oil m/e 413 |
| 63 | CH$_2$=C(CH$_3$)—CH$_2$— | pyrrolidine | 2-OCH$_3$-C$_6$H$_4$— | 4-OCH$_3$-C$_6$H$_4$— | — | —CH$_2$— | — | oil m/e 424 |
| 64 | CH$_2$=C(CH$_3$)—CH$_2$— | morpholine | Ph | Ph | — | —CH$_2$— | — | oil m/e 380 |
| 65 | CH$_2$=C(CH$_3$)—CH$_2$— | piperidine | Ph | Ph | — | —CH$_2$— | — | oil m/e 378 |

-continued $$R_4-A \quad \underset{\underset{R_5-Y-X}{|}}{N}-CH_2-CH-CH_2-O-R_1$$
$$\phantom{R_4-A\quad}\overset{R_3}{\underset{R_2}{\diagdown}}N$$

| No. | R₁ | R₂, R₃ | R₄ | R₅ | A | X | Y | |
|---|---|---|---|---|---|---|---|---|
| 66 | CH₂=C(CH₃)—CH₂— | —C₂H₅, —C₂H₅ | phenyl | phenyl | — | —CH₂— | — | Oxalate 61–63° C. ethyl acetate |
| 67 | (CH₃)₂C=CH—CH₂— | cyclic (pyrrolidine) | phenyl | phenyl | — | —CH₂— | — | Oxalate 149–150° C. ethyl acetate |
| 68 | CH₂=C(CH₃)—CH₂— | cyclic (pyrrolidine) | 4-OCH₃-phenyl | 4-OCH₃-phenyl | —CH₂— | —CH₂— | — | oil m/e 438 |
| 69 | CH₂=C(CH₃)—CH₂—CH₂— | cyclic (pyrrolidine) | phenyl | phenyl | — | —CH₂— | — | Oxalate 151–152° C. ethyl acetate |
| 70 | CH₂=CH—C(CH₃)₂— | cyclic (pyrrolidine) | phenyl | phenyl | — | —CH₂— | — | oil m/e 378 |
| 71 | (CH₃)₂—CH—CH₂— | cyclic (pyrrolidine) | phenyl | phenyl | — | —CH=CHCH₂— | — | Oxalate 119–120° C. ethyl acetate |

-continued $$R_4-A \overset{R_3}{\underset{R_5-Y-X}{N-CH_2-CH-CH_2-O-R_1}}$$

| No. | R1 | R2, R3 | R4 | R5 | A | X | Y | |
|---|---|---|---|---|---|---|---|---|
| 72 | (CH₃)₂—CH—CH₂— | ⌐ | phenyl | phenyl | — | CH₃<br>—CH—CH₃ | — | oil m/e 380 |
| 73 | phenyl | ⌐ | phenyl | phenyl | — | —CH₂— | — | Oxalate 136–137° C. ethyl acetate |
| 74 | 4-OCH₃-phenyl | ⌐ | phenyl | phenyl | — | —CH₂— | — | oil m/e 416 |
| 75 | 4-Cl-phenyl | ⌐ | phenyl | phenyl | — | —CH₂— | — | oil m/e 421 |
| 76 | phenyl | ⌐ | phenyl | 4-OCH₃-phenyl | — | —(CH₂)₂— | — | oil m/e 430 |

-continued $$R_4-A \diagdown \underset{R_5-Y-X}{N}-CH_2-\underset{\underset{R_2}{|}}{CH}-CH_2-O-R_1$$
$$\phantom{xxxxxxxxx} \underset{R_3}{|}$$

| No. | R1 | R2, R3 | R4 | R5 | A | X | Y | |
|---|---|---|---|---|---|---|---|---|
| 77 | (CH$_3$)$_2$—CH—CH$_2$— | ⌐⌐ | 4-OCH$_3$-C$_6$H$_4$— | 4-OCH$_3$-C$_6$H$_4$— | — | —(CH$_2$)$_2$— | — | oil m/e 440 |
| 78 | (CH$_3$)$_2$—CH—CH$_2$— | ⌐⌐ | 4-OCH$_3$-C$_6$H$_4$— | 4-OCH$_3$-C$_6$H$_4$— | — | —(CH$_2$)$_2$— | O | oil m/e 456 |
| 79 | (CH$_3$)$_2$—CH—CH$_2$— | ⌐⌐ | C$_6$H$_5$— | C$_6$H$_5$— | — | —(CH$_2$)$_4$— | — | oil m/e 408 |
| 80 | (CH$_3$)$_2$—CH—CH$_2$— | ⌐⌐ | 2-CH$_3$-pyridyl | 4-OCH$_3$-C$_6$H$_4$— | — | —CH$_2$— | — | oil m/e 411 |
| 81 | cyclopentyl-CH$_2$— | ⌐⌐ | C$_6$H$_5$— | C$_6$H$_5$— | — | —CH$_2$— | — | Fumarate 137–138° C. ethyl acetate |
| 82 | cyclopropyl-CH$_2$— | ⌐⌐ | C$_6$H$_5$— | C$_6$H$_5$— | — | —CH$_2$— | — | oil m/e 364 |

-continued $$R_4-A\diagdown_{N-CH_2-CH-CH_2-O-R_1}^{R_2\diagup^{R_3}}$$
$$R_5-Y-X$$

| No. | R₁ | R₂, R₃ | R₄ | R₅ | A | X | Y | |
|---|---|---|---|---|---|---|---|---|
| 83 | CH₂—CH₂—Ph | ⌐⌐ | Ph | Ph | — | —CH₂— | — | Oxalate 133–135° C. ethyl acetate |
| 84 | CH₂=C(CH₃)—CH₂— | ⌐⌐ | Ph | Ph | — | — | — | Oxalate 105° C. ethyl acetate |
| 85 | CH₃—C(CH₃)=CH—CH₂— | ⌐⌐ | Ph | thienyl-CH₂ | — | —CH₂— | — | Oxalate 118° C. ethyl acetate |
| 86 | CH₃—C(CH₃)=CH—CH₂— | ⌐⌐ | Ph | Ph | — | — | — | Oxalate 120° C. ethyl acetate |
| 87 | CH₂=C(CH₃)—CH₂—CH₂— | ⌐⌐ | Ph | 2-CH₃O-C₆H₄ | — | —CH₂— | — | Oxalate 108° C. ethyl acetate |
| 88 | CH₂=C(CH₃)—CH₂—CH₂— | ⌐⌐ | Ph | 4-CH₃O-C₆H₄ | — | —CH₂— | — | Oxalate 99° C. ethyl acetate |

-continued $$R_4-A \quad R_2 \quad R_3 \\ N-CH_2-CH-CH_2-O-R_1 \\ R_5-Y-X$$

| No. | R₁ | R₂, R₃ | R₄ | R₅ | A | X | Y | |
|---|---|---|---|---|---|---|---|---|
| 89 | CH₂=C(CH₃)—CH₂—CH₂— | ⌐⌐ | 4-OCH₃-C₆H₄— | 4-OCH₃-C₆H₄— | — | —(CH₂)₂— | — | Fumarate 105° C. ethyl acetate |
| 90 | CH₂=C(CH₃)—CH₂—CH₂— | ⌐⌐ | C₆H₅— | C₆H₅— | — | — | — | Oxalate 104° C. ethyl acetate |
| 91 | CH₂=CH—C(CH₃)₂— | ⌐⌐ | C₆H₅— | 2-OCH₃-C₆H₄— | — | —CH₂— | — | oil m/e 408 |
| 92 | CH₂=CH—C(CH₃)₂— | ⌐⌐ | C₆H₅— | 4-OCH₃-C₆H₄— | — | —CH₂— | — | Fumarate 148° C. ethyl acetate |
| 93 | CH₂=CH—C(CH₃)₂— | ⌐⌐ | C₆H₅— | 2-thienyl | — | —CH₂— | — | oil m/e 384 |

-continued $$R_4-A\underset{R_5-Y-X}{\overset{R_2\diagdown N\diagup R_3}{N-CH_2-CH-CH_2-O-R_1}}$$

| No. | R₁ | R₂, R₃ | R₄ | R₅ | A | X | Y | |
|---|---|---|---|---|---|---|---|---|
| 94 | CH₂=CH—C(CH₃)₂— | (ring) | phenyl | phenyl | — | — | — | Oxalate 135° C. ethyl acetate |
| 95 | CH₂=CH—C(CH₃)₂— | (ring) | 4-OCH₃-phenyl | 4-OCH₃-phenyl | — | —CH₂— | — | oil m/e 438 |
| 96 | CH₂=CH—C(CH₃)₂— | (ring) | 2-OCH₃-phenyl | 4-OCH₃-phenyl | — | —CH₂— | — | oil m/e 438 |
| 97 | CH₂=CH—C(CH₃)₂— | (ring) | 3,4-methylenedioxyphenyl | 4-OCH₃-phenyl | — | —CH₂— | — | oil m/e 452 |
| 98 | CH₂=C(CH₃)—CH₂— | (ring) | 2,6-dichlorophenyl | phenyl | — | —CH₂— | — | Fumarate 101° C. ethyl acetate |

-continued $$R_4-A\underset{R_5-Y-X}{\overset{R_2\diagdown N\diagup R_3}{N-CH_2-CH-CH_2-O-R_1}}$$

| No. | R₁ | R₂, R₃ | R₄ | R₅ | A | X | Y | |
|---|---|---|---|---|---|---|---|---|
| 99 | CH₂=C(CH₃)—CH₂— | ⌐⌐ | 2,4-(OCH₃)₂-C₆H₃— | C₆H₅— | — | —CH₂— | — | oil m/e 424 |
| 100 | CH₂=C(CH₃)—CH₂— | ⌐⌐ | 4-OC₂H₅-C₆H₄— | C₆H₅— | — | —CH₂— | — | oil m/e 408 |
| 101 | CH₂=C(CH₃)—CH₂— | ⌐⌐ | 4-OC₃H₇-C₆H₄— | C₆H₅— | — | —CH₂— | — | oil m/e 422 |
| 102 | CH₂=C(CH₃)—CH₂— | ⌐⌐ | 4-OCH(CH₃)₂-C₆H₄— | C₆H₅— | — | —CH₂— | — | oil m/e 422 |
| 103 | CH₂=C(CH₃)—CH₂— | ⌐⌐ | 4-OC(CH₃)₃-C₆H₄— | C₆H₅— | — | —CH₂— | — | Oxalate 128° C. ethyl acetate |

-continued
$$R_4-A \diagdown \underset{R_5-Y-X}{N-CH_2-CH-CH_2-O-R_1} \diagup \overset{R_3}{\underset{R_2}{N}}$$
| No. | $R_1$ | $R_2, R_3$ | $R_4$ | $R_5$ | A | X | Y | |
|---|---|---|---|---|---|---|---|---|
| 104 | $CH_2=\underset{CH_3}{\overset{\|}{C}}-CH_2-$ | 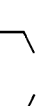 | 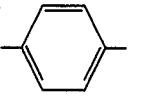 |  OCH₃ | — | —CH₂— | — | Oxalate 103° C. ethyl acetate |

In Vitro Test Results

Rat aorta segments were suspended in an organ bath and connected to a force pickup, and stretched to 15 mN. The KrebsHenseleit solution in the organ bath had the following composition:

NaCl=118 mM; KCl=4.7 mM; MgSO$_4$=1.2 mM; CaCl$_2$=2.5 mM; KH$_2$PO$_4$=1.2 mM; NaHCO$_3$=25 mM; glucose −11 mM.

The aorta segments were left in the bath for 45 minutes to reach equilibrium, and then a stock solution of KCl was added to the organ bath to increase the KCl concentration of the nutrient solution in the organ bath to 40 mM. After the aorta segments had been exposed for 30 minutes to the increased potassium concentration, the test substances were added at an identical concentration, (10$^{-6}$ mol/liter) to the bath solution. The test substances produced a relaxation effect which varied with the different test substances, and is reported in Table 1 below as a percent of the pre-contraction, determined 25 minutes after the test substance addition to the bath solution. The percent relaxation reported is a measure of the Ca++ antagonistic effect of the respective test substances. The higher the percent relaxation value reported in the right-hand column of Table 1, the more active the substance.

TABLE 1

% relaxation following pre-contraction with 40 mM K+ ions
Incubation time: 25 minutes
Concentration of the test compound: 10$^{-6}$ M/liter
Number of tested preparations per substance: n = 4

| Example No. | % relaxation |
|---|---|
| Bepridil (control) | 51 |
| 54 | 79 |
| 56 | 72 |
| 63 | 67 |
| 67 | 58 |
| 69 | 68 |
| 24 | 71 |
| 70 | 82 |
| 34 | 76 |
| 57 | 69 |

Bepridil = β-[2-Methylpropoxy)methyl]-N-phenyl-N-(phenylmethyl)-1-pyrrolidineethanamine.

As will be appreciated from Table 1, the compounds of the present invention are cardiovascular agents exhibiting antianginal and antiarrhythemic properties.

The compounds of the present invention may be administered to patients in a suitable amount, generally in an amount of 50 to 1000 mg per dose. The patient will normally be administered from 1 to 3 doses daily. The total daily dosage to the patient will typically be in the range of 1 to 40 mg/kg.

We claim:
1. Compound of the general formula:

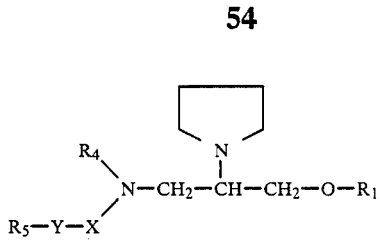

(I)

wherein R$_1$ is a straight-chained or branched C$_2$–C$_6$-alkenyl radical; R$_4$ is a phenyl radical which is unsubstituted or substituted at least once by C$_1$–C$_6$-alkyl, C$_2$–C$_6$-alkenyl, C$_1$–C$_3$-alkoxy, C$_2$–C$_6$-alkenyloxy, hydroxy-C$_1$–C$_6$-alkyl, C$_2$–C$_6$-alkylenedioxy, hydroxy-C$_1$–C$_3$-alkoxy, C$_1$–C$_3$ alkoxyethoxy, C$_1$–C$_6$-alkylamino, di(C$_1$–C$_6$-dialkyl)amino, C$_1$–C$_3$-alkoxycarbonylethyloxy, C$_1$–C$_6$-alkylthio, C$_1$–C$_6$-alkylsulphinyl, C$_1$–C$_6$-alkylsulphonyl, C$_1$–C$_6$-alkylsulphonyloxy, carboxy, C$_1$–C$_3$ alkoxycarbonyl, aminocarbonyl, mono- or di(C$_1$–C$_6$-alkyl)aminocarbonyl, halo-C$_1$–C$_6$-alkyl, cyano, or halogen; X is a straight-chained or branched, saturated or unsaturated aliphatic hyrocarbon radical containing up to 6 carbon atoms; Y is a valency bond or —O—; and R$_5$ is a phenyl radical which is unsubstituted or substituted at least once by C$_1$–C$_6$-alkyl, C$_1$–C$_3$-alkoxy, C$_2$–C$_6$-alkenyloxy, phenyl-C$_1$–C$_3$-alkoxy, hydroxy, hydroxy-C$_1$–C$_3$-alkoxy, C$_1$–C$_3$-alkoxy-C$_1$–C$_3$-alkoxy, C$_1$–C$_3$-alkoxycarbonyl-C$_1$–C$_3$-alkoxy, C$_1$–C$_2$-alkylenedioxy, di(C$_1$–C$_6$-alkyl)amino, C$_1$–C$_6$-alkylthio, C$_1$–C$_6$-alkylsulphinyl, C$_1$–C$_6$-alkylsulphonyl, C$_1$–C$_6$-alkylsulphonyloxy, hydroxy-C$_1$–C$_6$-alkyl, carboxy, C$_1$–C$_3$-alkoxycarbonyl, aminocarbonyl, mono- or di(C$_1$–C$_6$-alkyl)aminocarbonyl, cyano, or halogen; or a pharmacologically acceptable salt thereof.

2. Compound of claim 1, wherein R$_1$ is iso-C$_3$-C$_3$-alkenyl.

3. Compound of claim 1, wherein R$_1$ is methallyl or isopentenyl.

4. Compound of claim 1, wherein said compound is 2-(N-pyrrolidino)-3-methallyloxy-N-benzyl-N-(3,4-dioxymethylenephenyl)-propylamine or salt or isomer thereof.

5. Compound of claim 1, wherein said compound is 2-(N-pyrrolidino)-3-methallyloxy-N-phenyl-N-(4-methoxy-benzyl)propylamine or salt or isomer thereof.

6. Compound of claim 1, wherein said compound is 2-(N-pyrrolidino)-3-methallyloxy-N-(3-methoxy-phenyl)-N-(4-methoxy-benzyl)-propylamine or salt or isomer thereof.

7. Compound of claim 1, wherein said compound is 2-(N-pyrrolidino)-3-methallyloxy-N-(4-methoxy-phenyl)-N-(4-methoxy-benzyl)-propylamine or salt or isomer thereof.

8. Compound of claim 1, wherein said compound is 2-(N-pyrrolidino)-3-isopentenyloxy-N-phenyl-N-benzyl-propylamine or salt or isomer thereof.

9. A pharmaceutical composition suitable for the treatment of heart circulatory diseases comprising a therapeutically effective amount of a compound of claim 1 and a pharmaceutically acceptable carrier.

10. A method of producing a blood vessel relaxing effect in a patient in need of such effect, comprising administering to said patient a blood vessel relaxing amount of a compound of claim 1.

11. Method of claim 10, wherein said amount is 50 to 1000 mg per dose, administered 1 to 3 times a day.

* * * * *